US012582846B2

(12) United States Patent　　(10) Patent No.:　US 12,582,846 B2
Xiang et al.　　(45) Date of Patent:　Mar. 24, 2026

(54) ABSOLUTE IN VIVO RADIATION DOSIMETRY TOOL WITH XACT IMAGING

(71) Applicant: THE REGENTS OF THE UNIVERSITY OF CALIFORNIA, Oakland, CA (US)

(72) Inventors: Liangzhong Xiang, Irvine, CA (US); Leshan Sun, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 18/708,196

(22) PCT Filed: Nov. 7, 2022

(86) PCT No.: PCT/US2022/049167
　§ 371 (c)(1),
　(2) Date: May 7, 2024

(87) PCT Pub. No.: WO2023/081484
　PCT Pub. Date: May 11, 2023

(65) Prior Publication Data
　US 2025/0229107 A1　Jul. 17, 2025

Related U.S. Application Data

(60) Provisional application No. 63/276,952, filed on Nov. 8, 2021.

(51) Int. Cl.
　*A61N 5/10*　　　(2006.01)
　*A61B 5/00*　　　(2006.01)
　(Continued)

(52) U.S. Cl.
　CPC .......... *A61N 5/1071* (2013.01); *A61B 5/0093* (2013.01); *A61B 6/4258* (2013.01);
　(Continued)

(58) Field of Classification Search
　CPC ...... A61N 5/1071; A61B 5/0093; A61B 8/13; A61B 6/4258; A61B 6/5247; A61B 6/582
　See application file for complete search history.

(56) References Cited

U.S. PATENT DOCUMENTS 4,385,634 A　*　5/1983　Bowen ............... G01N 29/2418
　　　　　　　　　　　　　　　　　600/407
2012/0069962 A1　　3/2012　Fallone et al.
　(Continued)

FOREIGN PATENT DOCUMENTS

CN　　　　106178289 A　*　12/2016　........... A61B 5/0093
WO　　WO-2020227719 A1 *　11/2020　............... A61B 8/08

OTHER PUBLICATIONS

Xiang, Liangzhong, et al. "High resolution X-ray-induced acoustic tomography." Scientific reports 6.1 (2016): 26118. (Year: 2016).*
Lei, Hao, et al. "Toward in vivo dosimetry in external beam radiotherapy using x-ray acoustic computed tomography: A soft-tissue phantom study validation." Medical physics 45.9 (2018): 4191-4200. (Year: 2018).*
　(Continued)

*Primary Examiner* — Sean D Mattson
(74) *Attorney, Agent, or Firm* — FOLEY & LARDNER LLP

(57)　　　ABSTRACT

The present embodiments relate generally to increasing the precision of radiotherapy by measuring the absolute dose delivered to the tumor and surrounding normal tissue during the treatment. More particularly, some embodiments relate to an imaging reconstruction system for X-ray-induced acoustic computed tomography (XACT) using a model-based reconstruction method. Instead of reconstructing relative dose information for radiation beam localization, the system is capable of reconstructing absolute in vivo dose information. The XACT absolute in vivo dosimetry tool holds great potential for personalized cancer treatment and better outcomes. In some embodiments, thermal parameters, such as Gruneisen parameters, are used to convert reconstructed pressure information to dose. In addition, to avoid
　(Continued)

problems caused by electrical system gain, calibration tools, such as ion chambers, can be used to calibrate the system.

16 Claims, 10 Drawing Sheets

(51) Int. Cl.

| | |
|---|---|
| *A61B 6/00* | (2024.01) |
| *A61B 6/42* | (2024.01) |
| *A61B 6/58* | (2024.01) |
| *A61B 8/13* | (2006.01) |

(52) U.S. Cl.
CPC ............ *A61B 6/5247* (2013.01); *A61B 6/582* (2013.01); *A61B 8/13* (2013.01)

(56) References Cited

U.S. PATENT DOCUMENTS

| | | | |
|---|---|---|---|
| 2016/0074675 A1* | 3/2016 | Moskvin ................ | A61B 8/483 600/1 |
| 2017/0042428 A1* | 2/2017 | Kellnberger ....... | A61B 5/14551 |
| 2018/0344167 A1 | 12/2018 | Xiang et al. | |
| 2020/0041662 A1* | 2/2020 | Lu ....................... | G01T 1/20185 |

OTHER PUBLICATIONS

Dean-Ben, X. Luís, Vasilis Ntziachristos, and Daniel Razansky. "Acceleration of optoacoustic model-based reconstruction using angular image discretization." IEEE Transactions on medical imaging 31.5 (2012): 1154-1162. (Year: 2012).*
International Search Report and Written Opinion for PCT Application No. PCT/US2022/049167 dated Apr. 13, 2023.

* cited by examiner (a)
(b)
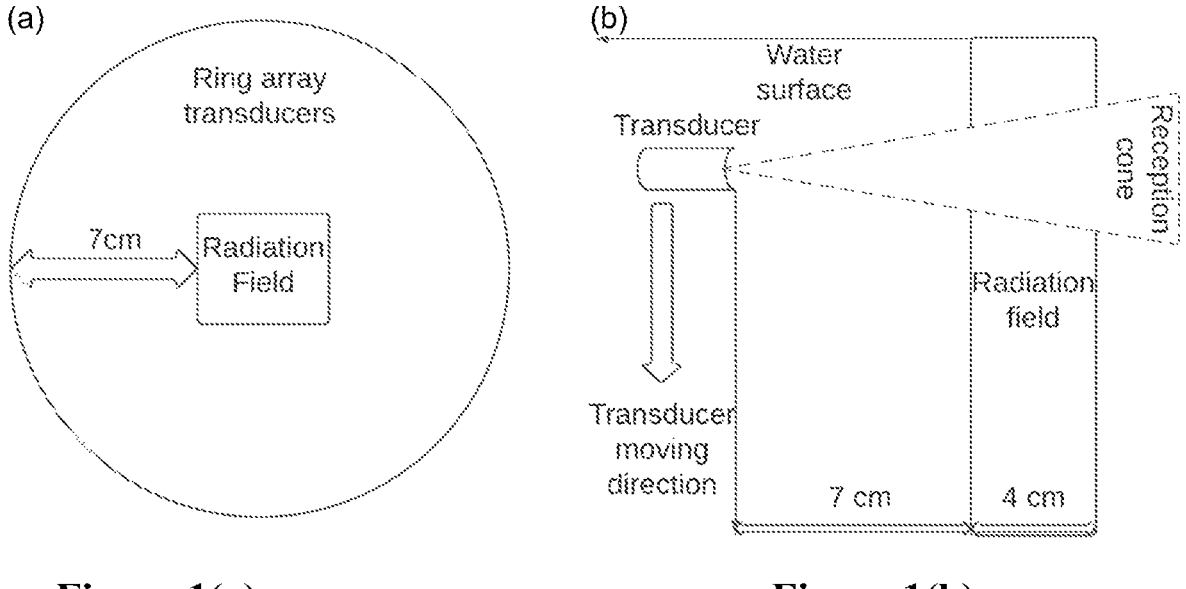
Figure 1(a)          Figure 1(b)

(a)

(b)

Water

Figure 5(a)                    Figure 5(b)
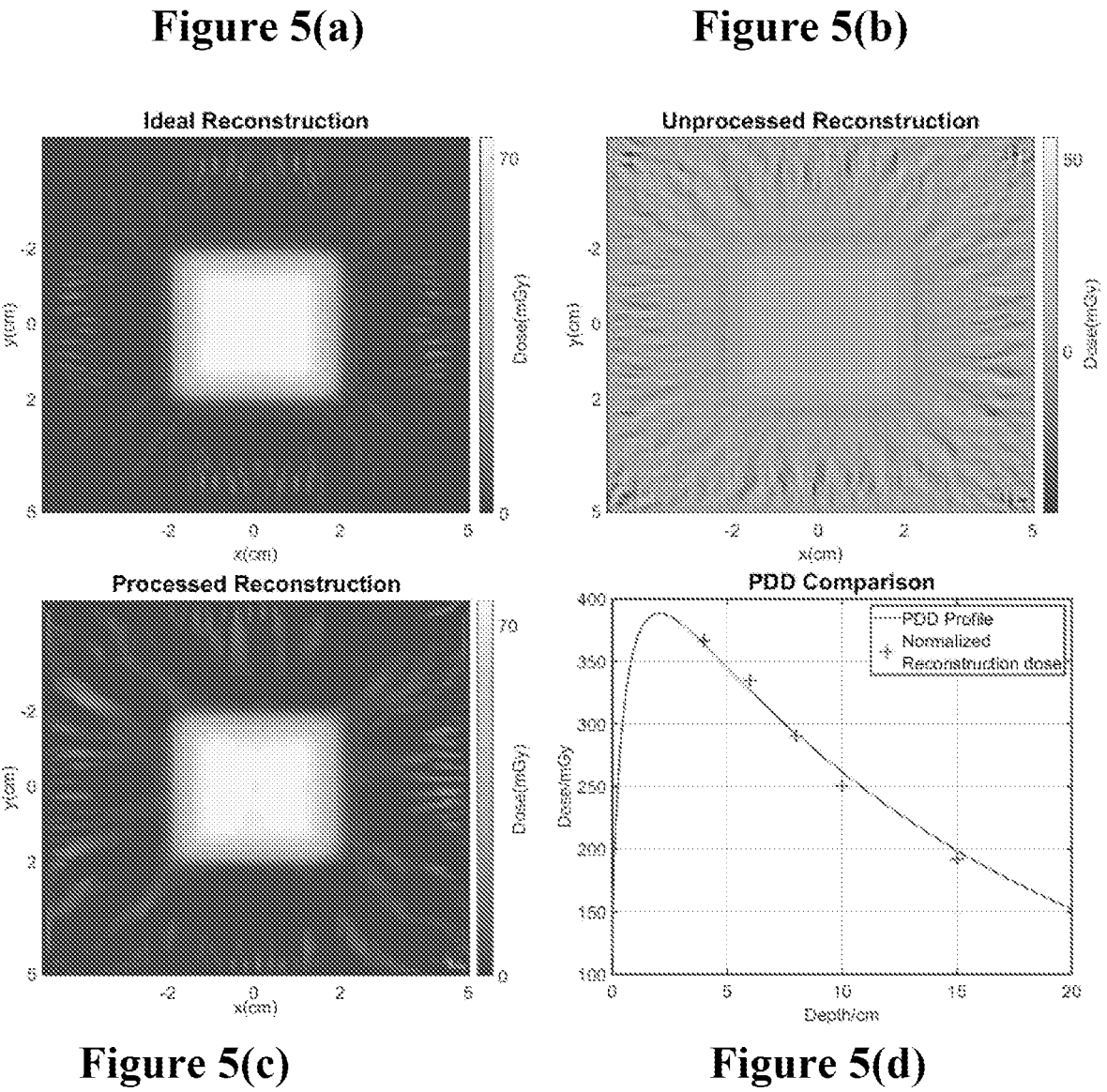
Figure 5(c)                    Figure 5(d)

Figure 8(a)          Figure 8(b)
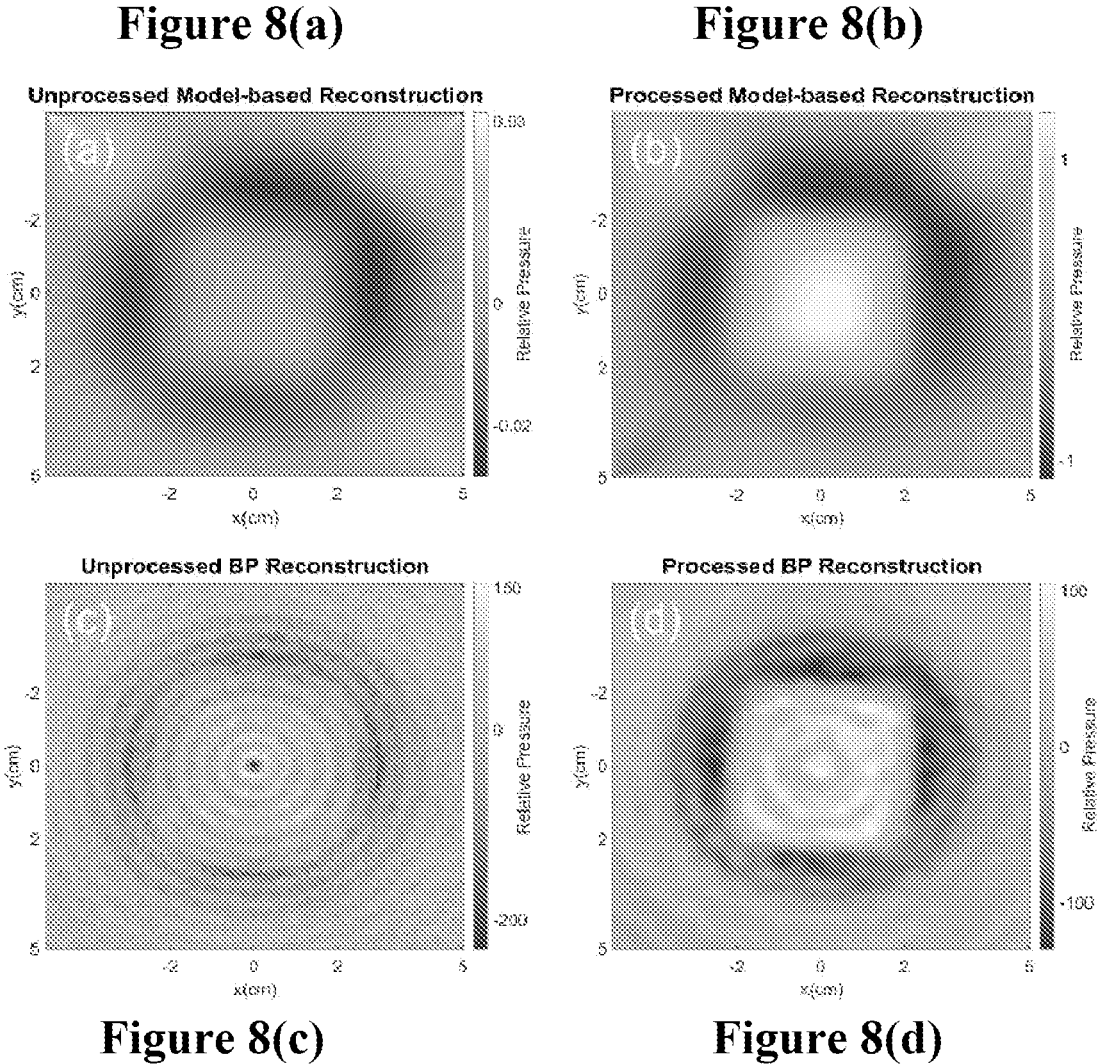
Figure 8(c)          Figure 8(d)

ABSOLUTE IN VIVO RADIATION DOSIMETRY TOOL WITH XACT IMAGING

CROSS-REFERENCE TO RELATED APPLICATIONS

The present application is a U.S. national stage application under 35 U.S.C. § 371 of International Application No. PCT/US2022/049167, filed on Nov. 7, 2022, which claims priority to U.S. Provisional Application No. 63/276,952 filed Nov. 8, 2021, the contents of which are incorporated by reference herein in their entirety.

STATEMENT OF GOVERNMENT SPONSORED RESEARCH

The present invention was made with government support under Award Number R37CA240806 awarded by the Nation Cancer Institute of the National Institutes of Health. The government has certain rights in the invention.

TECHNICAL FIELD

Embodiments relate generally to radiation therapy, X-ray induced acoustic computed tomography (XACT), X-ray beam tracking, absolute dosimetry; in vivo dosimetry and model-based image reconstruction algorithms.

BACKGROUND

In radiation therapy (RT), ionization radiation is used to damage malignant cells (Khan F M, Gibbons J P. Khan's the Physics of Radiation Therapy. Lippincott Williams & Wilkins; 2014). Patients undergoing RT will acquire planning computed tomography (CT) images for treatment planning purposes (Prince J L, Links J. Medical Imaging Signals and Systems. Prentice Hall; 2006). However, during each portion of treatment, uncertainties such as patient setup error, tumor shrinkage, and organ motion may affect the real dose delivered to the tumor and healthy cells (Height R, Khoo V, Lawford C, et al. The dosimetric consequences of anatomic changes in head and neck radiotherapy patients. Journal of Medical Imaging and Radiation Oncology. 2010; 54 (5): 497-504. doi: 10.1111/j.1754-9485.2010.02209.x; Shimohigashi Y, Toya R, Saito T, et al. Tumor motion changes in stereotactic body radiotherapy for liver tumors: an evaluation based on four-dimensional cone-beam computed tomography and fiducial markers. Radiat Oncol. 2017; 12 (1): 61. doi: 10.1186/s13014-017-0799-7). To address this problem, in-vivo radiation dosimetry tools are used to measure the radiation received by a patient during the time of treatment. In addition, with FLASH radiotherapy (Hughes J R, Parsons J L. FLASH Radiotherapy: Current Knowledge and Future Insights Using Proton-Beam Therapy. Int J Mol Sci. 2020; 21 (18): E6492. doi: 10.3390/ijms21186492) and stereotactic body radiation therapy (SBRT) (Alongi F, Arcangeli S, Filippi A R, Ricardi U, Scorsetti M. Review and Uses of Stereotactic Body Radiation Therapy for Oligometastases. Oncologist. 2012; 17 (8): 1100-1107. doi: 10.1634/theoncologist.2012-0092) becoming more and more popular, the very high dose delivery rate makes it more significant to precisely monitor the dose delivery during treatment.

To verify the treatment dose delivery, there are several tools that are currently used in clinics. On-board cone beam CT (CBCT) was mostly used in the clinic to evaluate and adapt the treatment plan (Paquin D, Levy D, Xing L. Multiscale registration of planning CT and daily cone beam CT images for adaptive radiation therapy. Medical Physics. 2009; 36 (1): 4-11. doi: 10.1118/1.3026602). However, CBCT images are acquired before the treatment starts and cannot monitor the dose delivery during treatment. To measure the real-time dose delivered to patients during treatments, various in-vivo radiation dosimetry tools were developed (Mijnheer B. State of the art of in vivo dosimetry. Radiation Protection Dosimetry. 2008; 131 (1): 117-122. doi: 10.1093/rpd/ncn231). Thermoluminescence detectors (TLDs) were developed to measure the radiation dose by detecting thermoluminescence light (Rivera T. Thermoluminescence in medical dosimetry. Applied Radiation and Isotopes. 2012; 71:30-34, doi: 10.1016/j.apradiso.2012.04.018). However, TLDs can only measure the dose received at one point on a patient. The dose integration capability makes film dosimetry a convenient tool for in-vivo dosimetry (Dogan N, Leybovich L B, Sethi A. Comparative evaluation of Kodak EDR2 and XV2 films for verification of intensity modulated radiation therapy. Phys Med Biol. 2002; 47 (22): 4121-4130. doi: 10.1088/0031-9155/47/22/314). However, its two-dimension limitation makes it only useful for relative dosimetry, despite its good spatial resolution. Electronic portal imaging device (EPID) has been considered to be capable of 3D in-vivo dosimetry, but it is difficult to map the EPID images into dose (Nailon W H, Welsh D, McDonald K, et al. EPID-based in vivo dosimetry using Dosimetry Check™: Overview and clinical experience in a 5-yr study including breast, lung, prostate, and head and neck cancer patients. Journal of Applied Clinical Medical Physics. 2019; 20 (1): 6-16. doi: 10.1002/acm2.12441). Therefore, the implementation of adaptive radiotherapy is limited by the lack of a 3D in-vivo device that can accurately measure the delivered dose to the patient.

In 2013, X-ray-induced acoustic tomography (XACT) was first proposed for biomedical purposes (Xiang L, Han B, Carpenter C, Pratx G, Kuang Y, Xing L. X-ray acoustic computed tomography with pulsed x-ray beam from a medical linear accelerator. Med Phys. 2013; 40(1):010701. doi: 10.1118/1.4771935). In XACT imaging, a pulsed x-ray excites a target and results in rapid localized heating (<mK). The abrupt temperature increase leads to thermoelastic expansion that causes differential pressure distribution. The local pressure difference causes the emission of a detectable acoustic wave in the ultrasound regime. The amplitude of the acoustic signal is proportional to the deposited heat energy, making it a potential tool for x-ray dosimetry. Furthermore, the induced X-ray acoustic (XA) wave propagates in all directions in 3D and can be detected at various transducer positions. Several research projects have been conducted to investigate the feasibility of using XACT for 3D real-time in-vivo dosimetry (Wang M, Samant P, Wang S, et al. Toward in vivo Dosimetry for Prostate Radiotherapy With a Transperineal Ultrasound Array: A Simulation Study. IEEE Transactions on Radiation and Plasma Medical Sciences. 2021; 5(3):373-382. doi:10.1109/TRPMS.2020.3015109; Forghani F, Mahl A, Patton T J, et al. Simulation of x-ray-induced acoustic imaging for absolute dosimetry: Accuracy of image reconstruction methods. Medical Physics. 2020; 47(3):1280-1290. doi:10.1002/mp.13961; Experimental evaluation of x-ray acoustic computed tomography for radiotherapy dosimetry applications—Hickling—2017—Medical Physics—Wiley Online Library. Accessed Sep. 2, 2021. |Scientific Reports. Accessed Sep. 8, 2021. XACT has numerous advantageous characteristics that make it a promising technique for water tank dosimetry applications. There is a linear relationship between deposited dose and induced pressure in a homogeneous medium. Additionally, XACT is dependent on the dose deposited per pulse, meaning it can be considered energy and dose rate independent. Also, XACT does not perturb the radiation beam provided the transducers are placed outside the beam path. These features of XACT simplify calibration and eliminate the need for many of the correction factors required by other dosimetry techniques.

Unlike conventional diagnostic acoustic imaging techniques that image the structure of tissue, the aim of XACT dosimetry is to image the acoustic sources induced by the x-ray dose deposition within the patient. Thus, quantitative in-tumor dosimetry could be possible by using XACT imaging if the parameters are properly modeled, and the transducer and amplification system is well calibrated and characterized. However, the current limitations in XACT imaging make it impossible to reconstruct absolute doses. One of the challenges in XACT imaging is the relatively long pulse duration (~4 µs) which would affect both the signal generation efficiency and imaging resolution. Deconvolution of the detected transducer signals from the LINAC pulse shape could be an interesting approach to resolve this problem. Another key challenge of XACT is its sensitivity to detecting small-amplitude acoustic waves. Improvements in detection amplification are needed to accurately image radiation fields without the need for excessive signal averaging. Additionally, deconvolution of the transducer's frequency response can further improve signal detection accuracy. More sophisticated signal processing and image reconstruction techniques are needed to obtain accurate XACT image reconstruction. Iterative time-reversal (ITR) algorithm has been proposed to quantitatively reconstruct dose information but lacks experimental validation.

It is against this technological backdrop that the present Applicant sought a technological solution to these and other issues deeply rooted in this technology.

SUMMARY

The present embodiments relate generally to increasing the precision of radiotherapy by measuring the absolute dose delivered to the tumor and surrounding normal tissue during the treatment. More particularly, some embodiments relate to an imaging reconstruction system for X-ray-induced acoustic computed tomography (XACT) using a model-based reconstruction method. Instead of reconstructing relative dose information for radiation beam localization, the system is capable of reconstructing absolute in vivo dose information. The XACT absolute in vivo dosimetry tool holds great potential for personalized cancer treatment and better outcomes. In some embodiments, thermal parameters, such as Gruneisen parameters, are used to convert reconstructed pressure information to dose. In addition, to avoid problems caused by electrical system gain, calibration tools, such as ion chambers, can be used to calibrate the system.

BRIEF DESCRIPTION OF THE DRAWINGS

These and other aspects and features of the present embodiments will become apparent to those ordinarily skilled in the art upon review of the following description of specific embodiments in conjunction with the accompanying figures, wherein:

FIG. 1. Illustration of 3D simulation setup. (a) Horizontal view of the simulation setup. 90 Transducers are distributed equally on the circle with 4 degrees angular interval. The radius of the circle is set to be 9 cm (the distance from transducer to the edge is 7 cm). The radiation field is a 4 cm by 4 cm square. (b) Vertical view of the simulation setup. The transducer is moving from the water surface to 20 cm depth under the water surface with 4 mm interval to form a cylindrical array. The reception cone of the transducer is set to be around 20 degrees according to the Olympus technical notes.

FIG. 5. Comparison of Reconstructed image using (a) ideal signal; (b) real simulated signal; (c) processed signal. (d) Comparison of the normalized reconstruct dose and the PDD profile.

FIG. 8. (a) Model-based reconstruction with unprocessed signal. (b) Model-based reconstruction with processed signal. (c) BP Reconstruction with unprocessed signal. (d) BP Reconstruction with processed signal FIG. 9. Model-based reconstruction at different depth (a) 6 cm; (b) 8 cm; (c) 10 cm. All three images are normalized using the maximum value in 6 cm-depth image.

DETAILED DESCRIPTION

Figure 2A:
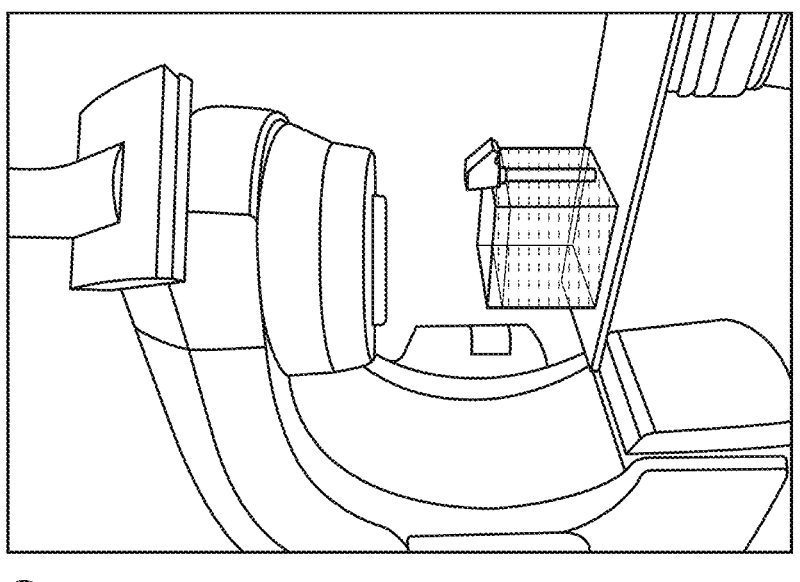
FIG. 2. Photograph of experimental set-up. (a) Water tank was placed on the LINAC couch. (b) The immersion ultrasound transducer was set to be able to move in z direction inside the water tank. The preamplifier and the DAQ system are not pictured in this photograph.

The present embodiments will now be described in detail with reference to the drawings, which are provided as illustrative examples of the embodiments so as to enable those skilled in the art to practice the embodiments and alternatives apparent to those skilled in the art. Notably, the figures and examples below are not meant to limit the scope of the present embodiments to a single embodiment, but other embodiments are possible by way of interchange of some or all of the described or illustrated elements. Moreover, where certain elements of the present embodiments can be partially or fully implemented using known components, only those portions of such known components that are necessary for an understanding of the present embodiments will be described, and detailed descriptions of other portions of such known components will be omitted so as not to obscure the present embodiments. Embodiments described as being implemented in software should not be limited thereto, but can include embodiments implemented in hardware, or combinations of software and hardware, and vice-versa, as will be apparent to those skilled in the art, unless otherwise specified herein. In the present specification, an embodiment showing a singular component should not be considered limiting; rather, the present disclosure is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present embodiments encompass present and future known equivalents to the known components referred to herein by way of illustration.

Purpose

Radiation dosimetry plays an important role in radiation therapy to ensure that radiation dose is accurately delivered to the tumor. Despite wide use in clinical intervention, the delivered radiation dose can only be planned and verified via simulation with phantoms, while in vivo and in-line verification of the delivered dose is still absent in the clinic, thereby making precision radiotherapy challenging. Among other things, the present Applicant has recently investigated X-ray-induced acoustic computed tomography (XACT) as an imaging method for use in in vivo dosimetry. While XACT has been studied for relative dosimetry, it has not been studied for its potential for absolute dosimetry. The aim of this study was to investigate the accuracy of XACT to reconstruct absolute dose in-tumor during radiotherapy.

Methods

A model-based image reconstruction algorithm was developed to quantify radiation dose in tumor using XACT imaging. In order to use XACT for absolute dosimetry measurements, the present embodiments deconvolute the effects of both the X-ray pulse shape and the finite frequency response of the ultrasound detector. Both 3D simulations and experimental measurements have been performed for in-tumor dosimetry with XACT imaging. Two imaging techniques, back projection and the developed model-based image reconstruction algorithm, are used to reconstruct the dose distribution, and have been compared throughout the simulations and experiments. The reconstructed dose was calibrated before comparing to the PDD profile. Experimental signal was acquired from a 4 cm×4 cm radiation field at depth of 6, 8, and 10 cm beneath the water surface. The acquired signal was processed before reconstruction to achieve accurate results.

Results

Applying a model-based reconstruction algorithm with non-negative constraints, the absolute radiation dose can be achieved in 3D simulations. The reconstructed absolute dose matches well with PDD profile after calibration in experiments. It has also been shown that XACT images can be displayed as pseudo color maps of acoustic intensity, which correspond to different radiation doses in the clinic.

Conclusions

Results show that the XACT imaging by model-base reconstruction algorithm is considerably more accurate than the dose reconstructed by back projection. With proper calibration, XACT is potentially applicable to the clinic for absolute in tumor dosimetry.

Introduction

In radiation therapy (RT), ionization radiation is used to damage malignant cells (Khan F M, Gibbons J P. *Khan's the Physics of Radiation Therapy*. Lippincott Williams &

Wilkins; 2014). To ensure that the ionization radiation can be delivered to the target without damaging benign cells, patients undergoing RT will acquire planning computed tomography (CT) images for treatment planning purposes (Prince J L, Links J. *Medical Imaging Signals and Systems*. Prentice Hall; 2006). However, the treatment plans are mostly generated using Monte Carlo simulations, which may not accurately represent the dose delivery as it cannot account for real-time information (Mohan R, Barest G, Brewster L J, et al. A comprehensive three-dimensional radiation treatment planning system. International Journal of Radiation Oncology*Biology*Physics. 1988; 15 (2): 481-495. doi: 10.1016/S0360-3016 (98) 90033-5). During each phase of treatment, uncertainties such as patient setup error, tumor shrinkage, and organ motion may affect the real dose delivered to the tumor and healthy cells (Height R, Khoo V, Lawford C, et al. The dosimetric consequences of anatomic changes in head and neck radiotherapy patients. *Journal of Medical Imaging and Radiation Oncology*. 2010; 54 (5): 497-504. doi: 10.1111/j.1754-9485.2010.02209.x; Shimohigashi Y, Toya R, Saito T, et al. Tumor motion changes in stereotactic body radiotherapy for liver tumors: an evaluation based on four-dimensional cone-beam computed tomography and fiducial markers. *Radiat Oncol*. 2017; 12 (1): 61. doi: 10.1186/s13014-017-0799-7). Tumors may not be effectively treated if only a limited dose is received, and healthy organs may be damaged if excessive dose is received. Adaptive radiotherapy (ART)—re-optimizing the treatment plan based on daily scans of the patient's anatomy in order to maintain or improve the plan quality—has been proposed as a method to allow for dose escalation. By capturing real-time in-vivo images of the delivered dose, a patient's treatment plan may be "adapted" over the course of treatment to reflect the changes in the patient anatomy. Recently, FLASH radiotherapy (Hughes J R, Parsons J L. FLASH Radiotherapy: Current Knowledge and Future Insights Using Proton-Beam Therapy. *Int J Mol Sci*. 2020; 21 (18): E6492. doi: 10.3390/ijms21186492) and stereotactic body radiation therapy (SBRT) (Alongi F, Arcangeli S, Filippi A R, Ricardi U, Scorsetti M. Review and Uses of Stereotactic Body Radiation Therapy for Oligometastases. *Oncologist*. 2012; 17 (8): 1100-1107. doi: 10.1634/theoncologist.2012-0092) have become popular for their effectiveness of cancer treatment. However, the very high dose delivery rate makes it more important to precisely monitor the dose delivery during treatment and requires new techniques for radiation dosimetry.

On-board cone beam CT (CBCT) was mostly used in-clinic to evaluate and modify the treatment plan. However, CBCT images are acquired before the treatment starts and cannot monitor the dose delivery during treatment. Therefore, various in-vivo radiation dosimetry tools were developed to measure the real-time dose during treatment (Mijnheer B. State of the art of in vivo dosimetry. *Radiation Protection Dosimetry*. 2008; 131 (1): 117-122. doi: 10.1093/rpd/ncn231). Thermoluminescence detectors (TLDs) can measure the radiation dose by detecting thermoluminescence light (Rivera T. Thermoluminescence in medical dosimetry. *Applied Radiation and Isotopes*. 2012; 71:30-34. doi: 10.1016/j.apradiso.2012.04.018). However, TLDs can only measure the dose received at one point on a patient. The dose integration capability makes film dosimetry a convenient tool for in-vivo dosimetry (Dogan N, Leybovich L B, Sethi A. Comparative evaluation of Kodak EDR2 and XV2 films for verification of intensity modulated radiation therapy. *Phys Med Biol*. 2002; 47 (22): 4121-4130. doi: 10.1088/0031-9155/47/22/314). Although it has good spatial resolution, it is limited to two dimensions and can only be used for relative dosimetry. Electronic portal imaging devices (EPIDs) have been considered to be capable for 3D in-vivo dosimetry but they have uncertainties when mapping the EPID images into dose (Nailon W H, Welsh D, McDonald K, et al. EPID-based in vivo dosimetry using Dosimetry Check™: Overview and clinical experience in a 5-yr study including breast, lung, prostate, and head and neck cancer patients. *Journal of Applied Clinical Medical Physics.* 2019; 20 (1): 6-16. doi: 10.1002/acm2.12441). Recently, Cherenkov emission was found to be useful for in vivo radiation dose mapping, and a radioluminescence imaging technique also was developed for quality assurance (QA), but this is only suitable for surface dosimetry applications. Therefore, the implementation of adaptive radiotherapy is limited by the lack of a real-time device that can accurately measure the delivered dose to deep tumor in the patient.

In 2013, X-ray-induced acoustic tomography (XACT) was first proposed for biomedical purposes (Xiang L, Han B, Carpenter C, Pratx G, Kuang Y, Xing L. X-ray acoustic computed tomography with pulsed x-ray beam from a medical linear accelerator. Med Phys. 2013; 40(1):010701. doi: 10.1118/1.4771935). In XACT imaging, a pulsed x-ray excites target and results in rapid localized heating (<mK). The abrupt temperature increase leads to thermoelastic expansion that causes differential pressure distribution. The local pressure difference causes the emission of a detectable acoustic wave in the ultrasound regime. The amplitude of the acoustic signal is proportional to the deposited heat energy, making it a potential tool for x-ray dosimetry. Furthermore, the induced X-ray acoustic (XA) wave is propagated in all directions in 3D and can be detected at various transducer positions. Various research projects have been conducted to investigate the feasibility of using XACT for 3D real-time in-vivo dosimetry (Wang M, Samant P, Wang S, et al. Toward in vivo Dosimetry for Prostate Radiotherapy With a Transperineal Ultrasound Array: A Simulation Study. *IEEE Transactions on Radiation and Plasma Medical Sciences.* 2021; 5(3):373-382. doi: 10.1109/TRPMS.2020.3015109; Forghani F, Mahl A, Patton T J, et al. Simulation of x-ray-induced acoustic imaging for absolute dosimetry: Accuracy of image reconstruction methods. *Medical Physics.* 2020; 47(3):1280-1290. doi: 10.1002/mp.13961; Experimental evaluation of x-ray acoustic computed tomography for radiotherapy dosimetry applications—Hickling—2017—Medical Physics—Wiley Online Library. Accessed Sep. 2, 2021. XACT has numerous advantageous characteristics that make it a promising technique for water tank dosimetry applications. There is a linear relationship between deposited dose and induced pressure in a homogeneous medium. Additionally, XACT is dependent on the dose deposited per pulse, meaning it can be considered energy and dose rate independent. Also, XACT does not perturb the radiation beam provided the transducers are placed outside the beam path. These features of XACT simplify calibration and eliminate the need for many of the correction factors required by other dosimetry techniques. Unlike conventional diagnostic acoustic imaging techniques that image the structure of tissue, the aim of XACT dosimetry is to image the acoustic sources induced by the x-ray dose deposition within the patient. Thus, quantitative in-tumor dosimetry could be possible by using XACT imaging if the parameters being properly modeled, and the transducer and amplification system is well calibrated and characterized. However, the current limitations in XACT imaging make it impossible to reconstruct absolute dose (Id.) One of the challenges in XACT imaging is the relative long pulse duration (~4 μs) which would affect both the signal generation efficiency and imaging resolution. Among other things, the present Applicant recognizes that deconvolution of the detected transducer signals from the linac pulse shape could be an interesting approach to resolve this problem.

Another key challenge of XACT is its sensitivity to detecting small amplitude acoustic waves. Improvements in detection amplification are needed to accurately image radiation fields without the need for excessive signal averaging. Additionally, deconvolution the transducer's frequency response can further improve signal detection accuracy. More sophisticated signal processing and image reconstruction techniques could be useful for obtaining accurate XACT image reconstruction. Iterative time-reversal (ITR) algorithm has been proposed to quantitatively reconstruct dose information but it lacks experimental validation.

In embodiments, mathematically modeled are the generation and propagation of XA signal and these models are used to quantitatively reconstruct 3D dose information (Dean-Ben X L, Ntziachristos V, Razansky D. Acceleration of Optoacoustic Model-Based Reconstruction Using Angular Image Discretization. *IEEE Transactions on Medical Imaging.* 2012; 31 (5): 1154-1162. doi: 10.1109/TMI.2012.2187460). Some embodiments deconvolute the effects of both the X-ray pulse shape and the finite frequency response of the ultrasound detector to improve the accuracy of XACT image reconstruction. Both 3D simulations and experimental measurements are performed for in-tumor dosimetry. The present embodiments use XACT to reconstruct 3D real-time absolute in-tumor dosimetry, which can potentially be used to monitor the dose received by tumor during treatment. The XACT reconstruction results have been validated with both simulation data and experimental data.

Materials and Methods

Generation and Propagation of X-Ray Induced Acoustic Wave

In XACT, an X-ray will cause temperature increases in its absorbing target, which will lead to the generation of acoustic signals (XA signals). The generation and propagation of XA signals under the assumptions of thermal confinement and zero acoustic attenuation can be expressed as:

$$\left(\nabla^2 - \frac{1}{c^2}\frac{\partial^2}{\partial t^2}\right)p(\vec{r}, t) = -\frac{\beta}{C_p}\frac{\partial H(\vec{r}, t)}{\partial t} \tag{1}$$

where $p(\vec{r},t)$ denotes the acoustic pressure at location $\vec{r}$ and time t, c is the speed of sound, $\beta$ is the thermal expansion coefficient, Cp denotes the target's heat capacity at a constant pressure, and $H(\vec{r},t)$ is the heating function.

The heat energy is related to the deposited radiation dose D and can be written as:

$$H = \eta_{th}D\rho \tag{2}$$

where $\eta_{th}$ is the percentage of dose energy converted into thermal energy and p is the density of the absorption target. Thus, equation (1) can be rewritten as:

$$\left(\nabla^2 - \frac{1}{c^2}\frac{\partial^2}{\partial t^2}\right)p(\vec{r}, t) = -\frac{\eta_{th}\rho\beta}{C_p}\frac{\partial D(\vec{r}, t)}{\partial t} \tag{3}$$

The dose deposited by the pulsed radiation will cause an abrupt increase in temperature. The right-hand side of equation (1) represents the thermal expansion caused from the temperature rising. The thermal expansion then becomes the source of acoustic wave, and its propagation is modeled by the left-hand side of equation (1).

Acoustic Forward Problem

The forward model deals with the prediction of the acoustic fields dominated by equation (3). The solution of equation (3) is given by (Xu M, Wang L V. Universal back-projection algorithm for photoacoustic computed tomography. *Phys Rev E Stat Nonlin Soft Matter Phys.* 2005; 71 (1 Pt 2):016706.

$$p(\vec{r}, t) = \frac{\Gamma\eta_{th}\rho}{4\pi c}\frac{\partial}{\partial t}\left(\frac{1}{ct}\int_{S(\vec{r},t)} D(\vec{r}, t)dS'(t)\right) \tag{4}$$

where $\Gamma(c^2\beta/C_p)$ is the Gruneisen parameter, S'(t) denotes a spherical surface that all points on the surface satisfy |r̄−r̄'|=ct. If the problem is 2D, S'(t) will reduce to a curved line that satisfies the same condition.

For certain absorption materials, the density, absorption rate and Gruneisen parameters are constant values. Therefore, one can set $$\frac{\Gamma\eta_{th}\rho}{4\pi c}$$

to be unity, and equation (4) can be further simplified as:

$$p(\vec{r}, t) = \frac{\partial}{\partial t}\left(\int_{S(\vec{r},t)} D(\vec{r}', t)d\theta\right) \tag{5}$$

To analytically solve the equation, discretization was performed by approximating surface S'(t) by a set of N points that are equally distributed according to space angles. Equation (5) can then be rewritten as:

$$p(\vec{r}, t) = \frac{I(t + \Delta t) - I(t + \Delta t)}{2\Delta t} \tag{6}$$

where I(t) is the discretized integration of D(r̄', t), and can be expressed as:

$$I(t) = \sum_{i=1}^{N} D(\vec{r}'_i, t)d\theta \tag{7}$$

By combining equations (6) and (7), the pressure at transducer position $\vec{r}_i$ and time $t_j$ $p(\vec{r}_i, t_j)$ can be expressed as a linear combination of the absorbed dose at positions $\vec{r}'_t$:

$$p(\vec{r}, t) = \sum_{i=1}^{N} a_t^{i,j} D(\vec{r}'_i, t) \tag{8}$$

where $a_t^{i,j}$ is the linear interpolation coefficients that was used to obtain D(r̄'ₜ,t).

With equation (8), the acoustic forward problem can be modeled as:

$$p = MD \tag{9}$$

where p is the pressure signal, M is the model matrix constitute of $a_t^{i,j}$, and D is the dose distribution map.

Image Reconstruction

The back-projection (BP) algorithms are commonly employed due to their simplicity and are easy to implement. However, the back-projection reconstruction only contains shape information and is inaccurate in quantification reconstruction. Therefore, to reconstruct dose information, model-based reconstruction was employed in this study and universal back-projection (UBP) reconstruction was used as a comparison.

The model-based reconstruction is based on the model matrix M computed as described here. M only depends on the geometry of the system setup and the characteristics of the material. Therefore, XACT image reconstruction is performed by minimizing the mean square difference between the theoretical pressure p and the measured pressure $p_m$.

$$D_{sol} = \arg\min_{D\geq 0} \|p_m - MD\|^2 \tag{10}$$

where $D_{sol}$ is the reconstructed dose map. D≥0 is the non-negative constraints for the reconstructed dose map (Clason C, Kaltenbacher B, Resmerita E. Regularization of Ill-Posed Problems with Non-negative Solutions. In: Bauschke H H, Burachik R S, Luke D R, eds. Splitting *Algorithms, Modern Operator Theory, and Applications.* Springer International Publishing; 2019:113-135. The non-negative constraints were lifted when investigating the shape of the field, and applied when doing quantitative reconstruction. The solution of (10) is given as (Pandey P K, Wang S, Aggrawal H O, Bjegovic K, Boucher S, Xiang L. Model-based X-ray Induced Acoustic Computed Tomography. *IEEE Trans Ultrason Ferroelectr Freq Control.* 2021; PP. doi:10.1109/TUFFC.2021.3098501):

$$D_{sol} = \left(M^T M + \lambda^2 R^T R\right)^{-1} M^T p_m \tag{11}$$

where R is the regularization matrix and $\lambda$ is the parameter for the regularization. In some embodiments, identity matrix is used for R as a Tikhonov regularization.

Simulation on Absolute Dosimetry in 3D

Simulation studies were performed by the present Applicant to test the feasibility of using XACT for absolute dose reconstruction. To simulate dose distribution, generated was a 4 cm×4 cm square radiation field using the LINAC percent depth-dose (PDD) profile in water.

As XA signals propagate in the form of spherical waves, a 3D cylindrical transducer array was used in order to receive full signal information. FIGS. 1(*a*) and 1(*b*) show the setup for the 3D cylindrical array simulation. FIG. 1(*a*) shows the horizontal view of the simulation setup. The radius of the cylinder is 9 cm and the center is set to be the radiation field's center. 90 transducers are arranged as a circle on one horizontal plane. FIG. 1(b) shows the vertical view of the simulation setup. There are 50 horizontal planes equally distributed from the water surface to 20 cm depth under the surface with 4 mm interval. Therefore, the cylindrical transducer array has 4500 transducers in total. No transducer is placed on top and bottom of the cylinder as it will block X-ray beam.

To simulate the real transducer, an angular directivity sensor was used (Rosnitskiy P, Yuldashev P, Khokhlova V. Effect of the angular aperture of medical ultrasound transducers on the parameters of nonlinear ultrasound field with shocks at the focus. *Acoustical Physics*. 2015; 61:301-307. doi:10.1134/S1063771015030148) in a forward signal simulation. The reception cone is shown in FIG. 1(b) and its angle was calculated to be 20° according to Olympus technical note (Yumpu.com. Ultrasonic Transducers Technical Notes—Olympus. yumpu.com. Accessed Sep. 2, 2021; The simulation signal was generated using the method described herein. The accuracy of the generated signal has been validated using a k-wave toolbox. Then the simulated 3D signal was reconstructed using both UBP method and model-based reconstruction method described herein. Both reconstruction results are compared to the initial dose distribution for analyzation.

Simulation on a Realistic Signal in 2D

It is not feasible to put one transducer at 4500 positions to acquire 3D signal information as it will take hundreds of hours and the radiation field will vary in day-to-day experiment. Therefore, a circular array simulation was performed which can be carried out clinically. The 2D simulation uses only one horizontal plane (e.g. 90) transducers' signals to perform the 2D reconstruction.

In addition, the simulated signal generated from the forward method is an ideal signal with infinite transducer bandwidth and infinite pulse duration. However, in real experiments, the LINAC X-ray pulse duration is about 4 μs and the transducer only has a narrow bandpass range. Both factors will largely affect the shape and amplitude of the XA signal.

To get a real simulated signal, first generated was a 4 μs square X-ray pulse and numerical convolution of the X-ray pulse was performed with the XA signal generated using equation (12):

$$p_{conv}(t) = \sum_{\tau=1}^{t} p(\tau)S(t-\tau) \quad (12)$$

where $p_{conv}$ is the convoluted signal, p is the ideal signal from equation (8), and S(t) is the LINAC X-ray pulse width. All terms are discretized for analytical calculation.

Then applied was a bandpass filter to the convoluted signal to simulate the signals that are detected by limited bandwidth transducer. The frequency spectrum of the bandpass filter is a gaussian function with a center frequency of 500 kHz and 100% bandwidth for −6 dB. The frequency spectrum was applied to the convoluted signal in frequency domain using equation (13):

$$p_{real}(t) = \mathcal{F}^{-1}(P(f) \times P(f)) \quad (13)$$

where $p_{real}$ is the detected signal with limited bandwidth transducer, P(f) is the Fourier transformation of $p_{conv}$, and F(f) is the gaussian frequency spectrum.

In the final process of the signal, both low frequency random noise and high frequency gaussian white noise were added to the signal to simulate the real scenario.

To perform image reconstruction with the real simulated signal, first applied were both low-pass and high-pass noise filters to eliminate the noise. Then the frequency spectrum is divided from the signal's frequency domain and deconvolution was performed to get the ideal signal. The reconstructed dose are normalized using PDD profile in order to compare and evaluate.

Experiment Workflow

Figure 2B:
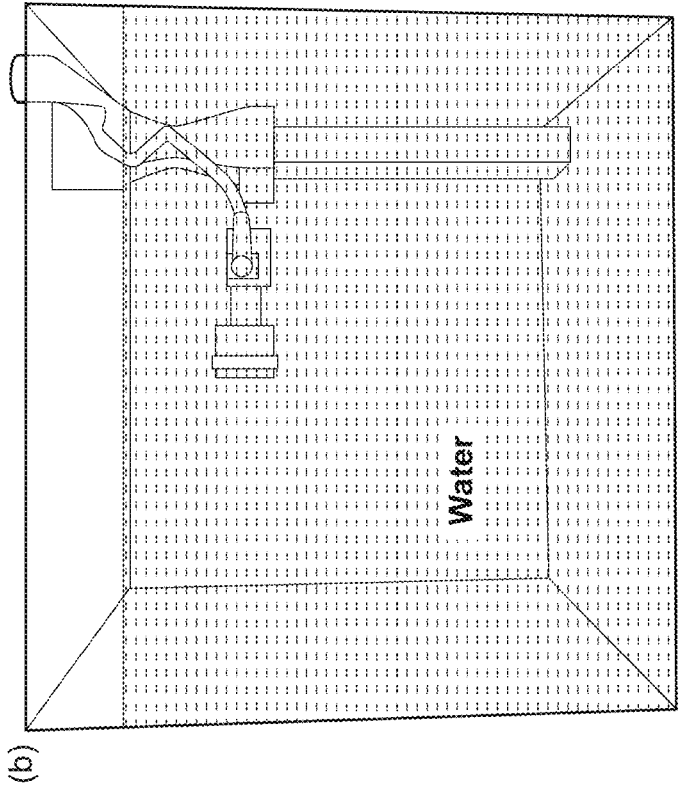

Experimental signals were acquired by irradiating a water tank using a clinical radiotherapy LINAC (Varian Medical Systems, Palo Alto, CA, USA). The radiation beam was set to be a 10 MV flattening filter free (FFF) photon beam produced by a True-Beam LINAC. The dose rate of LINAC was set to be 400 MU/min and the repetition rate is 120 Hz. FIGS. 2(a) and 2(b) Show the Experiment Setup. The Water Tank was Placed on the LINAC Couch at a Source to surface distance (SSD) of 100 cm.

The scheme of the experimental setup is similar to the illustration in FIGS. 1(a) and 1(b). The immersion ultrasound transducer with a central frequency of 0.5 MHz and −6 dB bandwidth of 80% was placed 9 cm away from the isocenter and the radiation field was set to be 4 cm×4 cm. However, instead of rotating the transducer in a circle, we choose to rotate LINAC collimator for 360" with 4" angular interval. In this way, the background noise caused by the movement of water can be greatly reduced.

The experimental signal was first processed according to the procedures described herein before doing the image reconstruction. Both UBP and model-based reconstruction were performed for comparison.

Results

3D Absolute Dosimetry

Figures 3A, 3B, 3C, 3D, 3E, 3F:
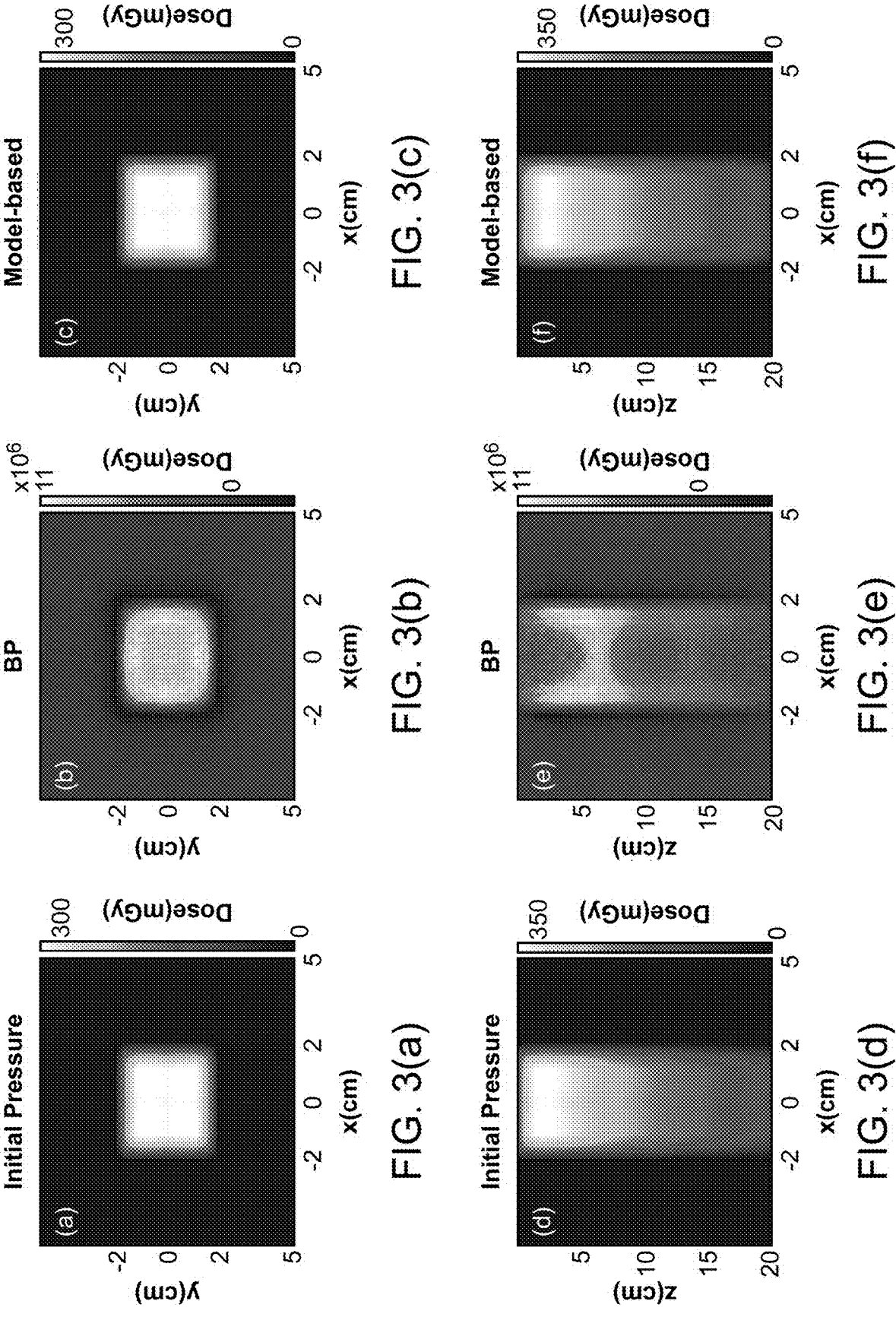
FIG. 3. Simulated 3D reconstruction. (a) Initial dose for horizontal plane. (b) Universal back-projection for horizontal plane. (c) Model-based reconstruction for horizontal plane. (d) Initial dose for vertical plane. (e) Universal back-projection for vertical plane. (f) Model-based reconstruction for vertical plane.

FIGS. 3(a) and 3(d) show the horizontal and vertical view of the generated initial dose distribution from LINAC PDD profile in water, respectively. The representative horizontal slice is taken at 6 cm depth. FIGS. 3(b) and 3(e) show the horizontal and vertical reconstructed UBP images, respectively. The shape of the radiation field is reconstructed well in the UBP images. However, the image quality of the UBP images on vertical view are apparently affected by the limited angular directivity of the signal. Only the horizontal slice at the center of the radiation beam has a good image quality. Nevertheless, the reconstructed dose range has a large difference from the original dose range. FIGS. 3(c) and 3(f) show the model-based reconstruction results for horizontal and vertical, respectively. The reconstructed dose distribution map matches well with the initial dose distribution map. There is a slight difference at the top and bottom of the vertical image. This is because transducers at the top and bottom have some part of their reception cones lies outside the image range, which causes the inaccuracy in the reconstructed images.

Recover True Dose Information with in a Realistically XA Signal

Figures 4A, 4B, 4C:
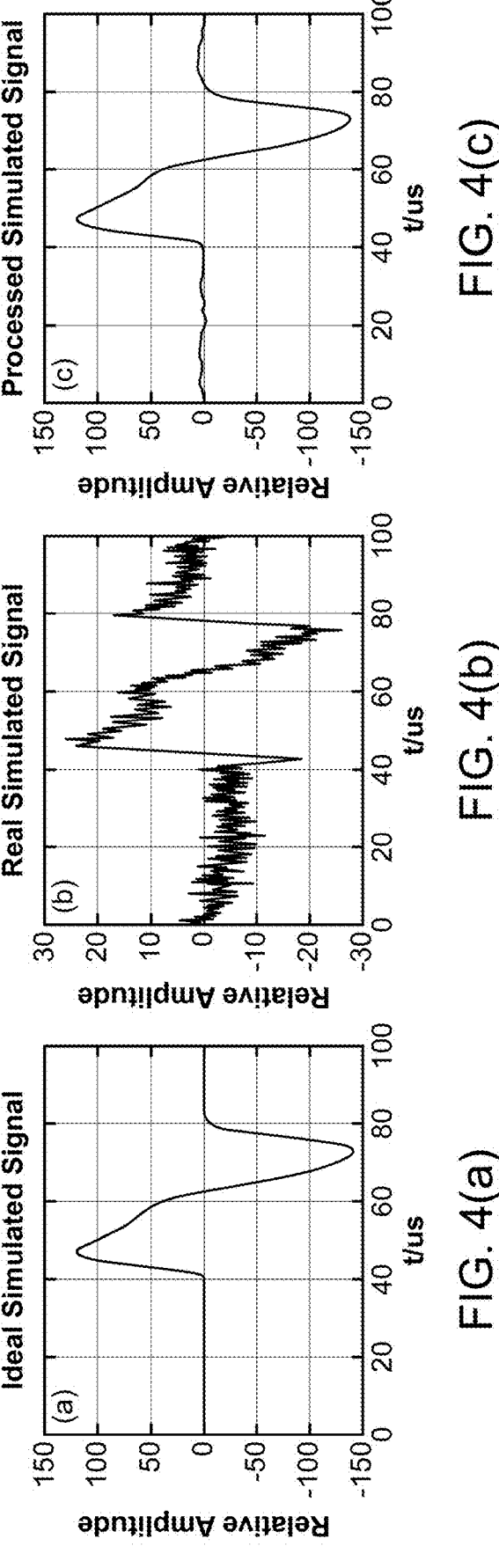
FIG. 4. Simulation signal comparison. (a) Ideal signal with no noise, very short pulse duration, and infinite bandwidth. (b) Real simulated signal with 4 µs x-ray pulse duration, 0.5 MHz center frequency bandpass filter, and 20 dB high and low frequency noise. (c) Processed signal using deconvolution and digital filter.

FIGS. 4(a) to 4(c) show the comparison of the simulated signals. The ideal signal demonstrated in FIG. 4(a) is extracted from the 3D simulation. It is generated with infinite bandwidth and x-ray pulse width. FIG. 4(b) shows the real simulated signal. The signal has been convoluted with 4 μs x-ray pulse and the 0.5 MHz central frequency response. 20 dB low and high frequency noises are added to the signal. FIG. 4(c) shows the processed simulated signal. A 20 kHz high-pass filter and a 200 kHz low-pass filter were first applied to eliminate the noise. Then the same frequency spectrum used in generating real simulated signal was divided in the frequency domain. In the end, deconvolution with the 4 µs x-ray pulse was performed to recover the ideal signal. The processed signal has similar shape as the ideal simulated signal. There is a slight difference between the processed signal and the ideal signal. This is because the low- and high-pass filter cannot fully eliminate the noise signal and there is signal information loss during bandpass process.

FIGS. 5(a) to 5(d) show the comparison between the reconstruction results using ideal simulated signal, real simulated signal and processed simulated signal. FIG. 5(a) is the reconstructed image at 6 cm depth under the water surface using ideal simulated signal. Despite some artifact around the image caused by the limited angular directivity of the transducer, the reconstruction shows clear shape of the radiation field. However, the dose range of the reconstruction is different from the initial pressure demonstrated in FIG. 3(a). This is because the simulated signal is generated in 3D while the reconstruction is performed in 2D. FIG. 5(b) shows the reconstructed image using the real simulated signal. The shape of the radiation field can barely be seen in the reconstruction. FIG. 5(c) shows the image reconstructed from processed signal. The limited-angle artifact was enlarged due to the presence of noise and the edge of the radiation field has a slight distortion. Overall, the shape of the reconstructed radiation field is satisfactory, and the range of the reconstructed dose is similar as FIG. 5(a). FIG. 5(d) shows the comparison between the reconstructed dose and the LINAC PDD profile. The 2D reconstructions were performed at depth 4, 6, 8, 10, and 15 cm. The reconstructed dose is normalized according to 4 cm depth. The reconstruction results align well with the PDD profile with slight difference caused from noise.

Experiment Result

Figures 6A, 6B, 6C:
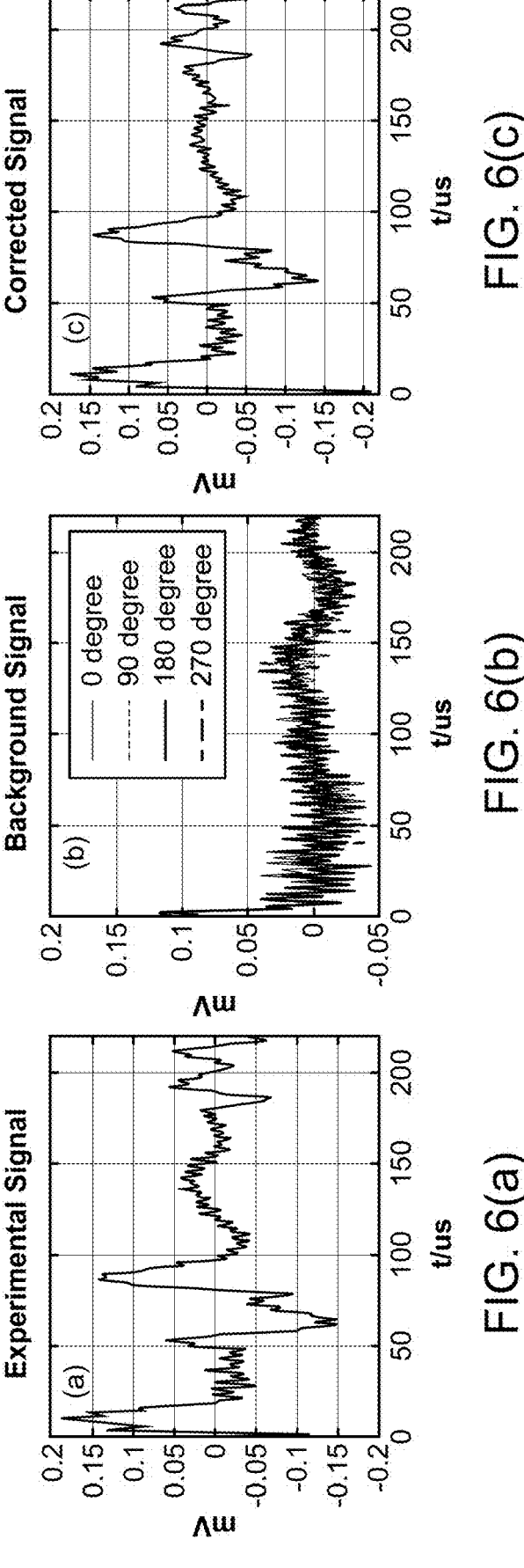
FIG. 6. (a) Acquired experimental signal with 1-300 kHz amplifier. (b) Background noise signal acquired at 4 different transducer positions: 0, 90, 180, 270. (c) Corrected signal with background noise signal deducted.

FIG. 6(a) shows the experimental signal acquired at 6 cm depth under the water surface. The signal was acquired by averaging 512 pulses and was amplified using 1-300 kHz amplifier. FIG. 6(b) shows the background noises that are acquired with LINAC collimator fully closed. The amplitude of the background noise in the figure cannot be neglected. In addition, the background signals are acquired at 4 field angles. It was noticed that noises at different positions varies to each other. Therefore, each background signal is deducted from the original signal according to the time. FIG. 6(c) shows the corrected signal that has the background signal deducted. The corrected signal clearly has near zero value outside of the XA signal range.

Figures 7A, 7B, 7C:
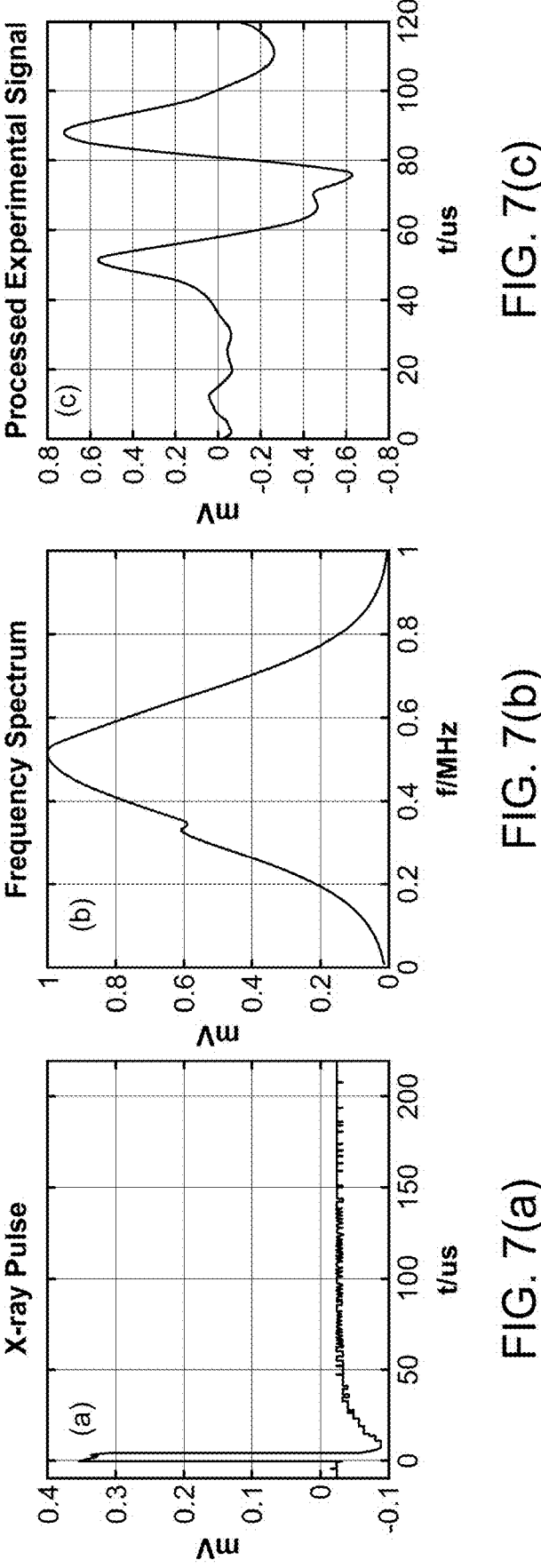
FIG. 7. (a) Transducer response for X-ray pulse. (b) Frequency spectrum for experiment transducer. (Acquired from Olympus instrumentation test) (c) Signal deconvoluted with x-ray pulse and frequency spectrum.

FIGS. 7(a) to 7(c) show the process of recovering the true XA signal. The corrected signal in FIG. 6(c) was first denoised using 20 kHz high-pass and 200 kHz low-pass digital filters. FIG. 7(a) shows the X-ray pulse reading from separate channel of the transducer. This pulse signal was deconvoluted from the denoised signal. FIG. 7(b) shows the frequency spectrum acquired from Olympus instrumentation test. It is then divided from the deconvoluted signal in the frequency domain. FIG. 7(c) shows the processed experimental signal. The XA signal shape can be clearly observed in the processed signal plot.

FIGS. 8(a) to 8(d) show the reconstruction results using both the unprocessed and processed experimental signal. It is noticed that the relationship between signal unit mV and the real dose is unclear. Therefore, relative pressure was used in the reconstruction results. FIG. 8(a) is the unprocessed model-based reconstruction. Only a shadow of the radiation field can be seen in the center, which is similar to the simulation result in FIG. 5(b). With the processed signal, the reconstruction is much better in FIG. 8(b). The UBP reconstruction using unprocessed signal shown in FIG. 8(c) is strongly affected by the high frequency noise. There are some improvements in the UBP reconstruction using processed signal, but artifacts still exist in the center of the radiation field.

Figures 9A, 9B, 9C:
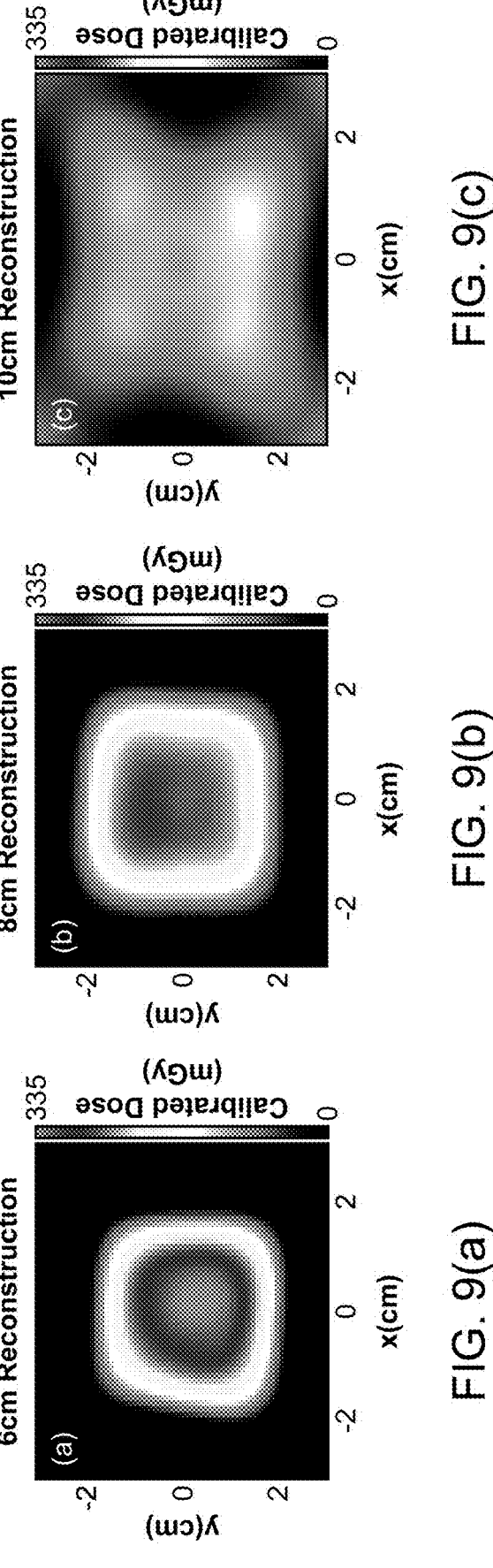

In order to see the quantitative dose reconstruction, acquired were three signal sets at 6, 8, and 10 cm. The reconstruction results are shown in FIGS. 9(a) to 9(c). Here, it was chosen to use the PDD profile to calibrate the relative pressure, thus the results are shown in dose. There is a good reconstruction for the signal acquired at 6 and 8 cm as the signal is very strong. However, with the 10 cm signal, a good reconstruction could not be obtained as the signal to noise ratio becomes too small. Nevertheless, one can still get a good radiation field shape in 10 cm reconstruction. In addition, the reconstructed dose is decreasing with the transducer depth increasing, which matches the simulation results.

The reconstruction system can be built for each specific XACT signal acquiring system such as planar array or circular array. The inverse acoustic model can be computed and stored for reconstruction purposes.

Figure 10:
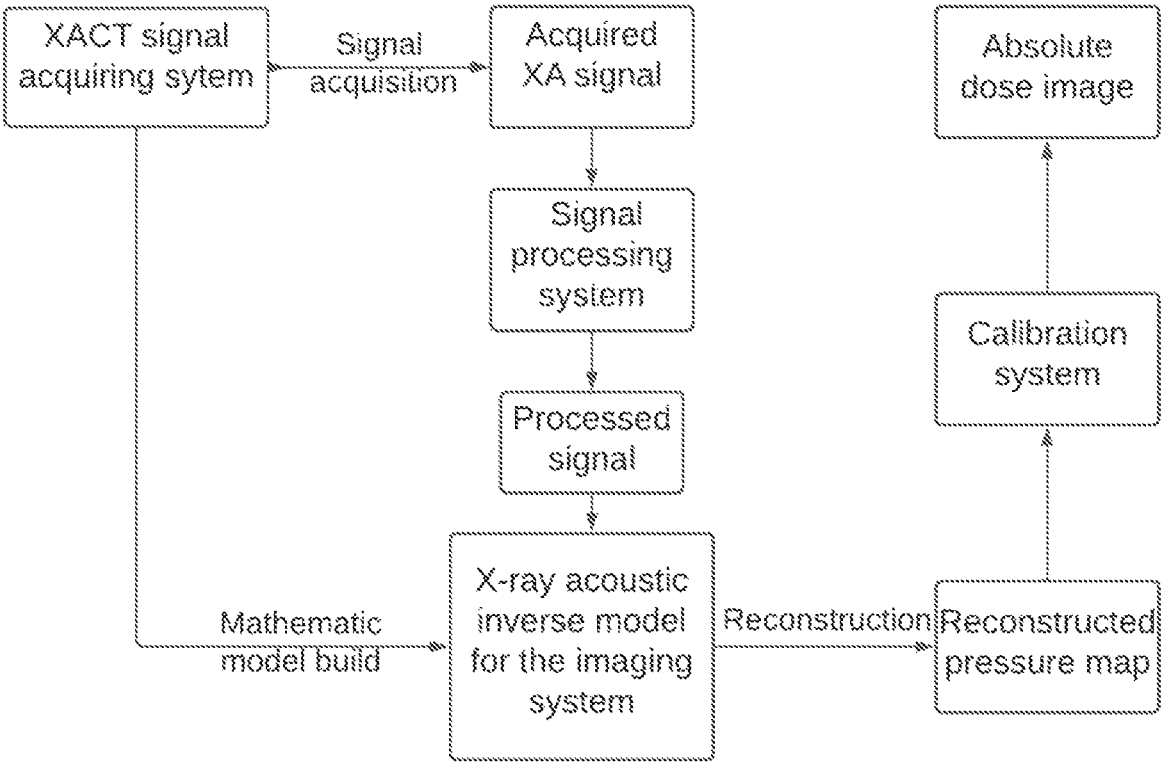
FIG. 10 illustrates an example workflow of an XACT imaging system according to embodiments.

In addition, the reconstructed image from equation (11) is an acoustic pressure image, which needed to be converted to dose image using thermal parameters. However, to map the converted dose image to absolute dose image, it is preferred to calibrate the system, which is presented in FIG. 10 below, illustrating an example workflow of an XACT imaging system according to embodiments. Some embodiments use percent depth-dose (PDD) profile in water from LINAC system as a calibrator. Further efforts should be used to calibrate the system when imaging tissues.

Discussion

This work first investigated the feasibility of using XACT for 3D absolute dosimetry in radiation therapy. A discretized mathematical model was used to simulate the generation and propagation of the XA wave. For the detection of XA signal, considered was the reception angle of the real transducer instead of using infinite angular directivity. For the reconstruction of XACT images, previous work mainly used a BP algorithm (High Resolution X-ray-Induced Acoustic Tomography|Scientific Reports. Accessed Sep. 8, 2021. However, the BP algorithm is oversimplified as it only sums the radial projections for each transducer, which cannot quantify the dose. Therefore, employed was a model-based algorithm to better reconstruct the quantitative dose information.

A first simulation created a 4 cm×4 cm radiation field in water using PDD profile from LINAC. The 3D reconstruction result (FIGS. 3(a) to 3(f)) Shows that Model-Based algorithm performs better than the UBP algorithm in localizing the radiation field. In addition, the reconstructed dose matches the initial dose distribution quantitatively.

However, in clinic, it is not feasible to have a 3D transducer array that covers the whole radiation field. Therefore, a second simulation tried to perform the dose reconstruction in 2D with a circular array. In addition, the XA signal is generated from LINAC X-ray pulse which has a longer pulse duration than laser and cannot be seen as delta pulse. The transducer used to collect the XA signal also has a limited bandwidth. In the 2D simulation, these properties were taken into account and the real simulated signal was generated that matches the experimental signal. The comparison between the real simulated signal and the ideal signal (FIGS. 4(*a*) to 4(*c*)) shows the shapes and the amplitudes of the two signals varies a lot.

The 2D reconstruction results (FIGS. 5(*a*) to 5(*d*)) show that, in order to reconstruct accurate radiation field, the detected real signal must be processed before doing the reconstruction. In addition, it was noticed that the reconstructed dose is different from the initial dose distribution for the representative plane. This is because the XA signal propagates in 3D and 2D transducer array can only get partial signals. Therefore, calibration should be performed to acquire absolute dosimetry. In embodiments, the PDD at 6 cm depth is used to calibrate the reconstructed dose at the corresponding 2D plane. After the calibration, the quantified dose matches well with the PDD profile.

For experimental study, acquired was a ring array XA signal from a single transducer by rotating the LINAC head for 360°. This strategy can avoid the water motion caused by rotating transducer in the water tank. However, acquiring data from 90 radiation field positions can be time-consuming and the LINAC output can vary from time to time. Therefore, background signals are acquired at different experiment time points to lower the effects of the background noise. In addition, it was chosen to place the transducer 9 cm away from the center of the radiation field to avoid head wave caused by x-ray directly hitting the transducer, which can be viewed in FIGS. 6(*a*) to 6(*c*). Although the head wave may still affect the signal at 9 cm distance, one cannot move it further as tests show that the signal-to-noise ratio will decrease rapidly after 9 cm.

To recover the ideal XA signal, LINAC x-ray pulse duration and transducer frequency spectrum were acquired experimentally and through documentation, respectively. The reconstruction result (FIGS. 8(*a*) to 8(*d*)) accurately localized the radiation field and have a uniform dose distribution in the center of the radiation field. However, one cannot get absolute dosimetry information directly from the reconstruction as one cannot calculate the relationship between signal amplitude (mV) and dose (Gy).

To quantify the reconstructed dose in experimental results, PDD profile was used to calibrate the images. From the reconstructed images for different depths (FIGS. 8(*a*) to 8(*d*)), one can clearly see the dose is decreasing with depth increasing. However, the reconstructed dose cannot match the PDD profile well after the calibration. This is because one cannot fully eliminate the affection of noises.

With the rapid development of radiation therapy, more complex dose delivery plans are made, and higher dose delivery rate are applied. Therefore, it is needed to measure the real delivered dose to ensure the precision of the treatments. As the strength of X-ray acoustic signals is proportional to the delivered dose and it propagates spherically, XACT can potentially be used to monitor the dose delivered to certain volume during treatment. Furthermore, XACT technique is non-invasive, making it easy to implement by placing transducers around the patient during radiotherapy and no treatment procedures are subjected to change.

However, to apply XACT to a clinic environment, it is needed to build a complete data acquisition system to recover ideal XA signal from the system gain and background noise. Additional embodiments can include an XACT system to get a strong and noise-free signal. In addition, calibration can be used for the XACT to reconstruct absolute dose. PDD profile used in the present disclosure is an efficient tool for calibration. Furthermore, the present disclosure used a full-view data acquisition scheme to reconstruct accurate XACT images. However, it is often impractical to employ full-view acquisition in clinic. Therefore, new transducer arrays, such as transperineal planar array, can be used for clinical purposes.

CONCLUSIONS

Demonstrated herein is the capability of using XACT for absolute dosimetry in a simulation study. Applied was a model-based algorithm to XACT modality that has a better performance than universal back-projection algorithm in the reconstruction of quantitative dose information. Furthermore, it was demonstrated that the experimental XA signal can be used for dose reconstruction if calibrated. Therefore, XA imaging has a great potential to be used as absolute dosimetry in radiation therapy.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably coupleable," to each other to achieve the desired functionality. Specific examples of operably coupleable include but are not limited to physically mateable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

Although the present embodiments have been particularly described with reference to preferred examples thereof, it should be readily apparent to those of ordinary skill in the art that changes and modifications in the form and details may be made without departing from the spirit and scope of the present disclosure. It is intended that the appended claims encompass such changes and modifications.

What is claimed is:

1. A system comprising:
a signal acquisition block coupled to receive a signal from a X-ray-induced Acoustic Computed tomography (XACT) system while a dose is being applied to a target; and
an image reconstruction block configured to produce an absolute dose image from the received signal, the absolute dose image corresponding to the dose being applied to the target,

wherein the image reconstruction block uses a matrix of linear interpolation coefficients that represent a geometry of a setup of the system and characteristics of a material of the target to reconstruct the absolute dose image from the received signal.

2. The system of claim 1, wherein the image reconstruction block uses thermal parameters to convert reconstructed pressure information to dose.

3. The system of claim 2, wherein the thermal parameters include Gruneisen parameters.

4. The system of claim 1, further comprising calibration tools to compensate for problems caused by electrical system gain.

5. The system of claim 4, wherein the calibration tools include an ion chamber.

6. The system of claim 1, wherein the absolute dose image provides information for a radiotherapy dose delivered in vivo to a tumor and surrounding tissue during a treatment.

7. The system of claim 1, wherein the image reconstruction block is configured to perform a model-based reconstruction method using the matrix of linear interpolation coefficients as a model.

8. The system of claim 1, wherein the received signal includes pressure measurements obtained from a plurality of transducers arranged around the target.

9. A method comprising:
acquiring a signal from a X-ray-induced Acoustic Computed tomography (XACT) system while a dose is being applied to a target; and
generating an absolute dose image from the received signal, the absolute dose image corresponding to the dose being applied to the target,
wherein generating the absolute does image includes using a matrix of linear interpolation coefficients that represent a geometry of a setup of the system and characteristics of a material of the target to reconstruct the absolute dose image from the received signal.

10. The method of claim 9, wherein generating the absolute dose image includes using thermal parameters to convert reconstructed pressure information to dose.

11. The method of claim 9, wherein the acquired signal is an X-ray-induced acoustic (XA) signal.

12. The method of claim 9, further comprising performing calibration to compensate for problems caused by electrical system gain.

13. The method of claim 9, wherein the absolute dose image provides information for a radiotherapy dose delivered in vivo to a tumor and surrounding tissue during a treatment.

14. The method of claim 9, wherein generating the absolute dose image includes performing a model-based reconstruction method using the matrix of linear interpolation coefficients as a model.

15. The method of claim 14, wherein performing the model-based reconstruction includes using the acquired signal that has been processed using signal processing.

16. The method of claim 14, wherein performing the model-based reconstruction includes generating a reconstructed pressure map.

* * * * *